United States Patent
Dockendorf

(10) Patent No.: US 11,033,936 B2
(45) Date of Patent: Jun. 15, 2021

(54) METHOD AND APPARATUS FOR SORTING PIECES

(71) Applicant: Karl Paul Dockendorf, Jacksonville, FL (US)

(72) Inventor: Karl Paul Dockendorf, Jacksonville, FL (US)

( * ) Notice: Subject to any disclaimer, the term of this patent is extended or adjusted under 35 U.S.C. 154(b) by 181 days.

(21) Appl. No.: 16/288,101

(22) Filed: Feb. 28, 2019

(65) Prior Publication Data

US 2019/0262867 A1 Aug. 29, 2019

Related U.S. Application Data

(60) Provisional application No. 62/636,235, filed on Feb. 28, 2018.

(51) Int. Cl.
*B07C 5/36* (2006.01)
*A61L 2/10* (2006.01)
*B07C 5/342* (2006.01)

(52) U.S. Cl.
CPC ............... *B07C 5/342* (2013.01); *A61L 2/10* (2013.01); *B07C 5/36* (2013.01); *B07C 5/363* (2013.01); *A61L 2202/11* (2013.01)

(58) Field of Classification Search
CPC ........ A61L 2/10; A61L 2201/11; B07C 5/342; B07C 5/36; B07C 5/363
USPC ......................................... 209/552, 576, 580
See application file for complete search history.

(56) References Cited

U.S. PATENT DOCUMENTS

| | | | | |
|---|---|---|---|---|
| 2,075,731 A * | 3/1937 | Laesch | ...................... | B03B 5/02 209/422 |
| 2,607,480 A * | 8/1952 | Dauber | .................... | B07C 5/06 209/643 |
| 2,874,841 A * | 2/1959 | Peterson | ................. | B07B 1/286 209/329 |
| 2,970,693 A * | 2/1961 | Morris | ..................... | A24B 3/18 209/265 |
| 4,289,241 A * | 9/1981 | Litrap | ....................... | B03B 5/02 209/44 |
| 4,289,270 A * | 9/1981 | Warsinske | ................ | B04B 1/02 494/27 |
| 4,339,043 A * | 7/1982 | Tice | .......................... | B03B 5/26 209/251 |
| 4,697,709 A * | 10/1987 | Codding | ................. | B07C 5/366 209/549 |
| 5,275,294 A * | 1/1994 | Krenzler | ................. | B07B 13/11 209/434 |

(Continued)

OTHER PUBLICATIONS

Joseph Zhu, "Automatic Lego sorting machine based on Raspberry Pi", https://www.youtube.com/watch?v=7oz4uBisCt0, Oct. 22, 2017.

(Continued)

*Primary Examiner* — Terrell H Matthews

(57) ABSTRACT

A novel consumer grade automatic sorter for pieces is disclosed with an application to organizing interlocking toy brick systems. The invention of a novel means to propel and separate pieces, and process sensor data in combination with standard methods for binning and storage. A novel mechanical screw is proposed to propel the parts. The device comprises a novel combination of backgrounds and artificial intelligence/machine learning to enable sensing of colors, estimation of size, and transparency of pieces. In addition, a method to embed a neural network efficiently on a microcontroller is disclosed.

17 Claims, 9 Drawing Sheets

(56) References Cited

U.S. PATENT DOCUMENTS

| | | | | |
|---|---|---|---|---|
| 5,421,461 | A | * | 6/1995 | Ruzic ................... B03B 5/02 209/332 |
| RE36,537 | E | * | 2/2000 | Sommer, Jr. ......... B07C 5/3416 209/576 |
| 6,991,132 | B1 | * | 1/2006 | Berryman .......... A46B 11/0024 222/103 |
| 7,469,557 | B2 | * | 12/2008 | Griffin ................ G01N 30/52 65/55 |
| 7,893,378 | B2 | * | 2/2011 | Kenny ................ B07B 11/04 209/576 |
| D757,142 | S | * | 5/2016 | Pung ...................... D15/147 |
| 9,715,058 | B1 | * | 7/2017 | Zhang ................ G02B 6/0036 |
| 2006/0016735 | A1 | * | 1/2006 | Ito ...................... B07C 5/366 209/576 |
| 2014/0284255 | A1 | * | 9/2014 | Hug .................... B07C 5/3427 209/587 |
| 2018/0029085 | A1 | * | 2/2018 | Justice ................ B07C 5/3425 |
| 2020/0164383 | A1 | * | 5/2020 | Valerio ................. B07B 1/26 |

OTHER PUBLICATIONS

Jacques Mattheij, "Sorting 2 Metric Tons of Lego", https://jacquesmattheij.com/sorting-two-metric-tons-of-lego/, Apr. 29, 2017.
"The Best Lego Sorting Machines You Will See", The Technic Gear, http://thetechnicgear.com/2014/02/best-lego-sorting-machines-will-see/, Feb. 28, 2014.
"Lego Sort and Store", Lego, https://www.amazon.com/d/Toy-Building-Sets/LEGO-KP001-Lego-Sort-Store/B005L0MKS4.

* cited by examiner

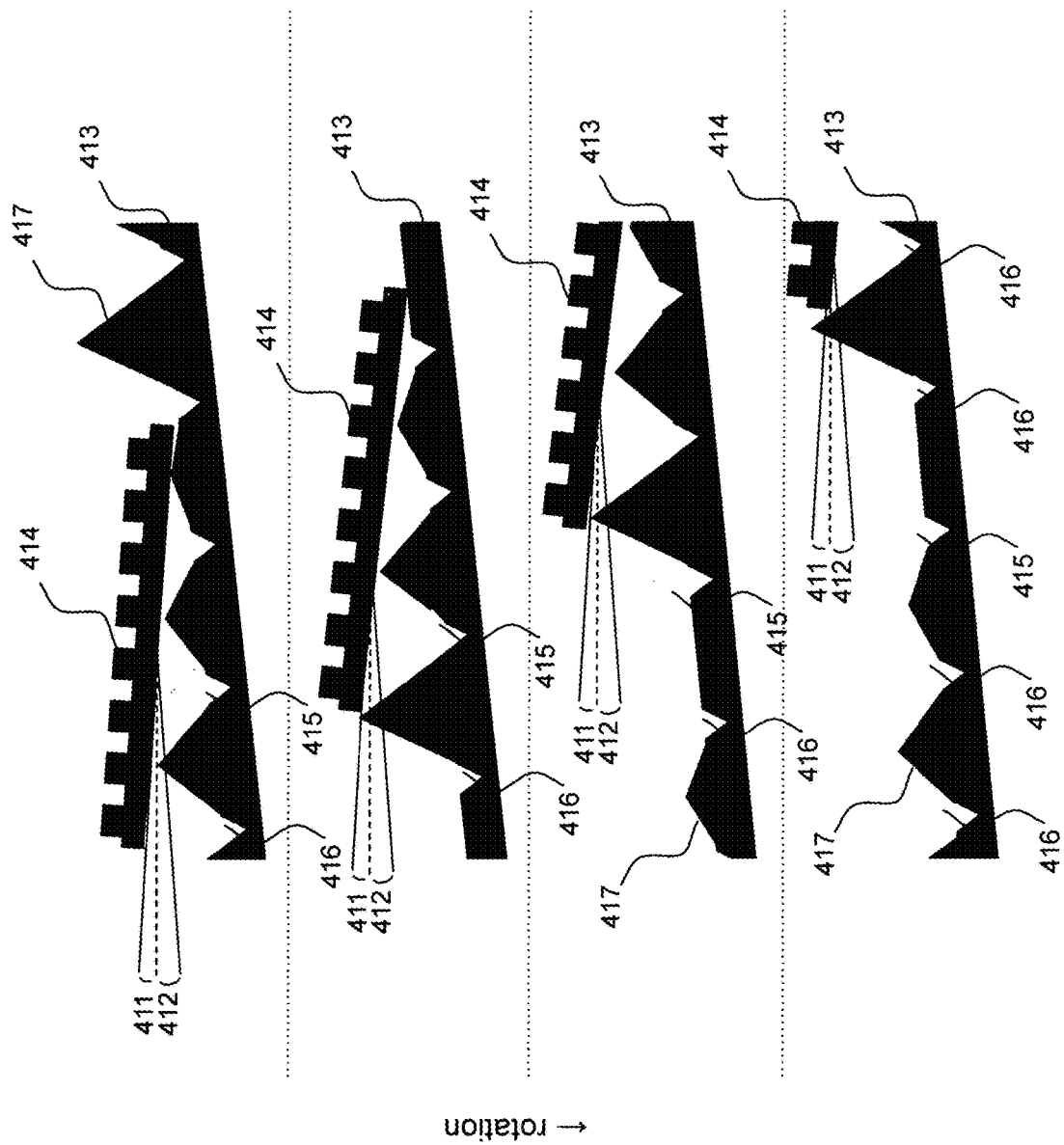

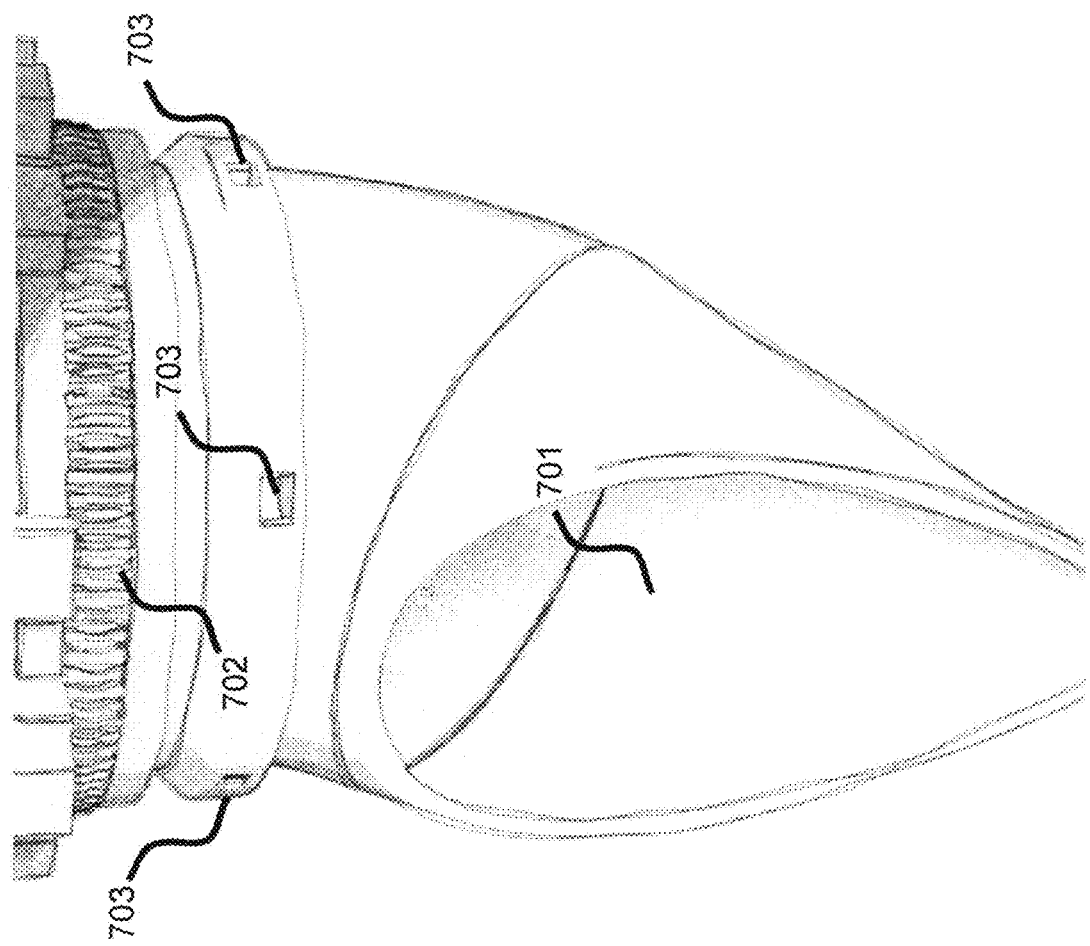

METHOD AND APPARATUS FOR SORTING PIECES

CROSS-REFERENCE TO RELATED APPLICATIONS

This application claims the benefit of U.S. Provisional Application No. 62/636,235 filed on Feb. 28, 2018 titled METHOD AND APPARATUS FOR SORTING SMALL COLORED PIECES, the contents of which is hereby incorporated by reference herein in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS)

Not Applicable

STATEMENT REGARDING PRIOR DISCLOSURES BY THE INVENTOR OR A JOINT INVENTOR

Not Applicable

BACKGROUND OF THE INVENTION

Every week the average household spends over 4 hours cleaning up and organizing their home. For children, this process can take a long time to perform adequately with small pieces. It also can be a barrier to playtime for children with obsessive compulsive disorders (OCD). Playtime is a necessary component to childhood, aiding the development of 3D comprehension and manipulation. Interlocking toy brick systems provide great value in this development; however, they tend to pose difficulty with cleanliness and organization as hundreds of parts are typically left on the floor after play. This requires a significant time investment by the parents and/or children to remedy. In addition, the more pieces that are owned, the harder it is (and longer it takes) to find the desired pieces to build with, unless they are organized, which requires upfront time and consistent additional time investment during cleaning and organization that has to be done manually. Either way, the more pieces that are owned increases the time overhead of playing with large collections of interlocking brick systems.

BRIEF SUMMARY OF THE INVENTION

We propose a novel consumer grade automatic sorter for small pieces. Applications are wide ranging which may include everything from interlocking brick systems to hard candy to hardware (nuts, bolts, screws, etc), but is not limited to those and the invention includes being scaled up. With respect to interlocking brick systems, an automatic color sorter aids the most common method for organizing pieces and can eliminate most of the organization time and burden for the use of large collections of pieces. This is made possible through the invention of a novel means to propel and separate pieces, and process sensor data in combination with standard methods for binning and storage. From a mechanical perspective, the device uses gravity and a novel combination of shape, motion and vibration to propel the pieces, and a spigot to quickly divert pieces to different locations. From a sensor and electrical perspective, the device can use lighting and one or more sensors to measure the color components of pieces. In addition, the device uses a novel combination of backgrounds and artificial intelligence/machine learning to enable sensing of colors, estimation of size, and transparency of pieces.

BRIEF DESCRIPTION OF THE SEVERAL VIEWS OF THE DRAWINGS

A more complete understanding of the apparatus and system of the present invention may be had in reference to the following Drawings.

Figure 1:
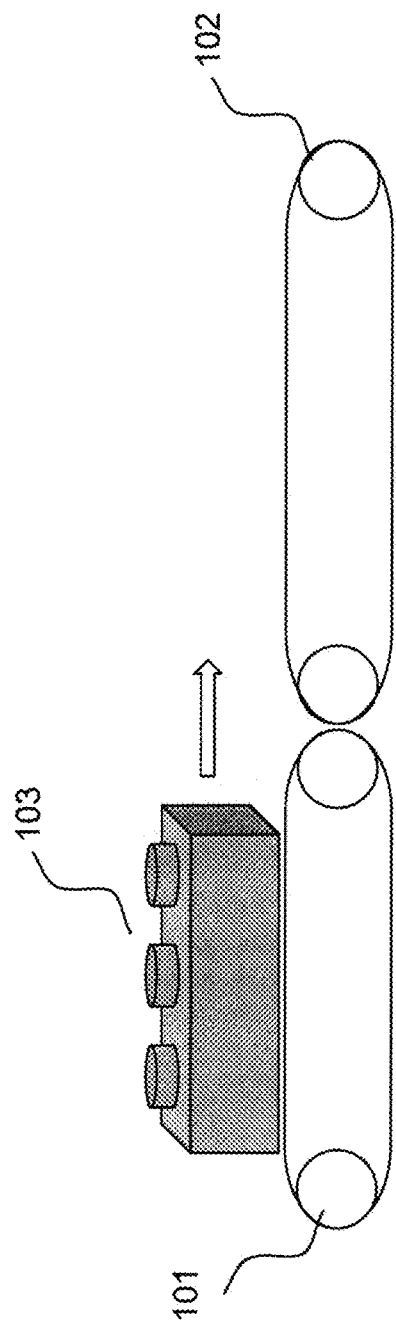
FIG. 1 is a depiction of a dual conveyor separating embodiment.
Figure 2:
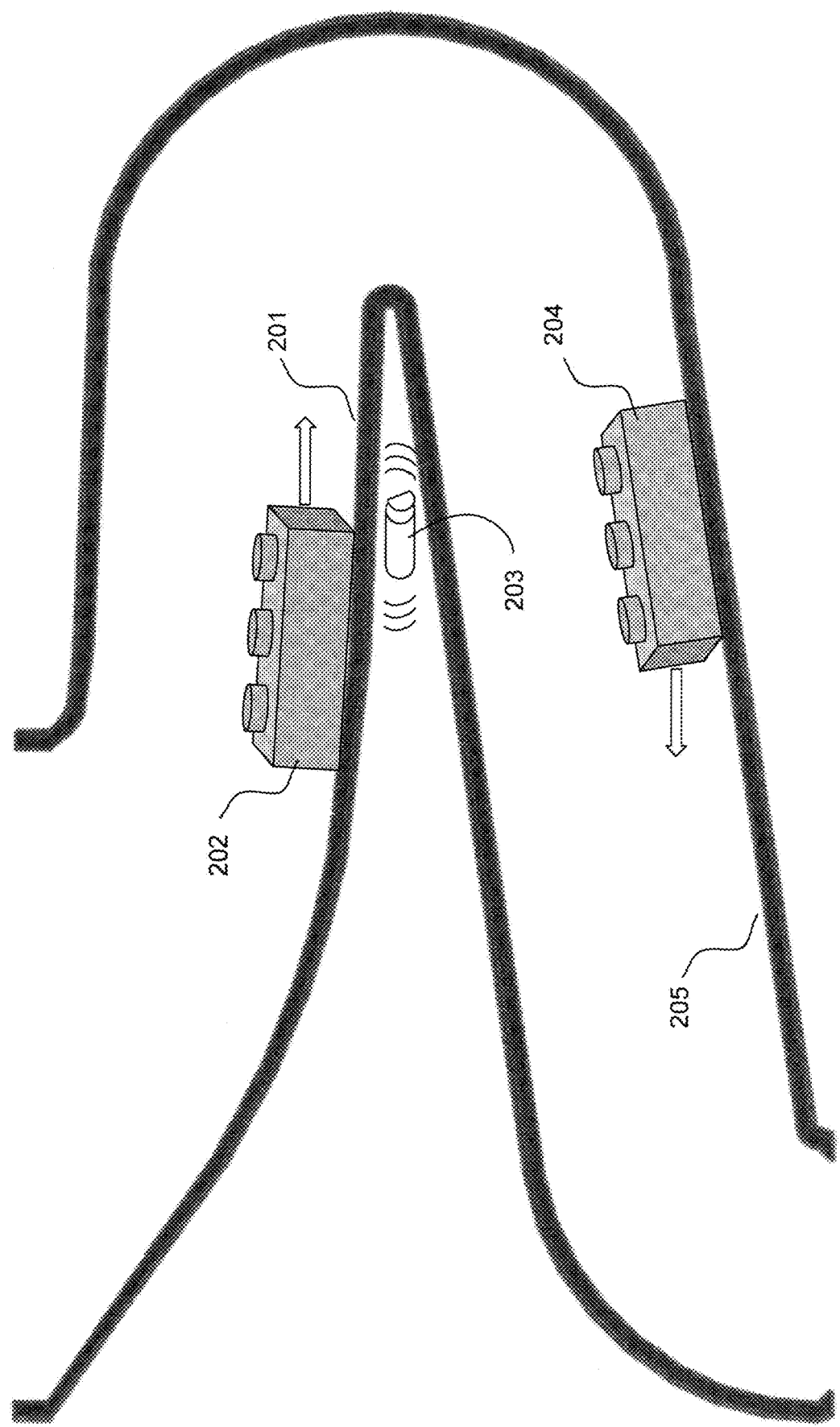
FIG. 2 is a depiction of a dual slide separating embodiment.

The mechanisms of FIG. 1 and FIG. 2 may be intermixed for a conveyor/slide or slide/conveyor separators. These are possible alternatives to the preferred separator mechanism.

Figure 3A:
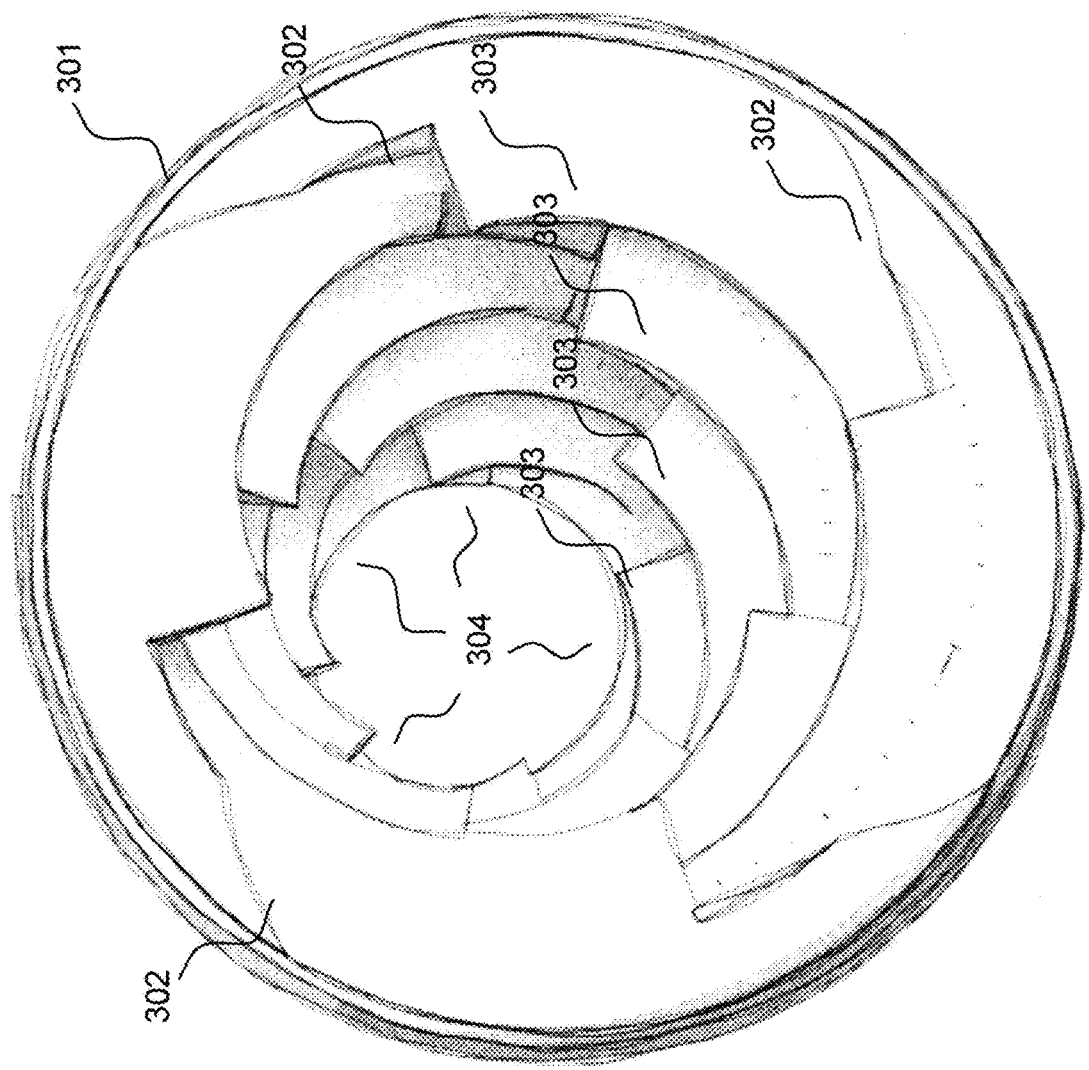

FIG. 3A is a rendering of the inventive tube screw as viewed down the central axis. The shallow helical grooves are shown with the larger intermittent ramps between extending from the crests of the screw.

Figure 3B:
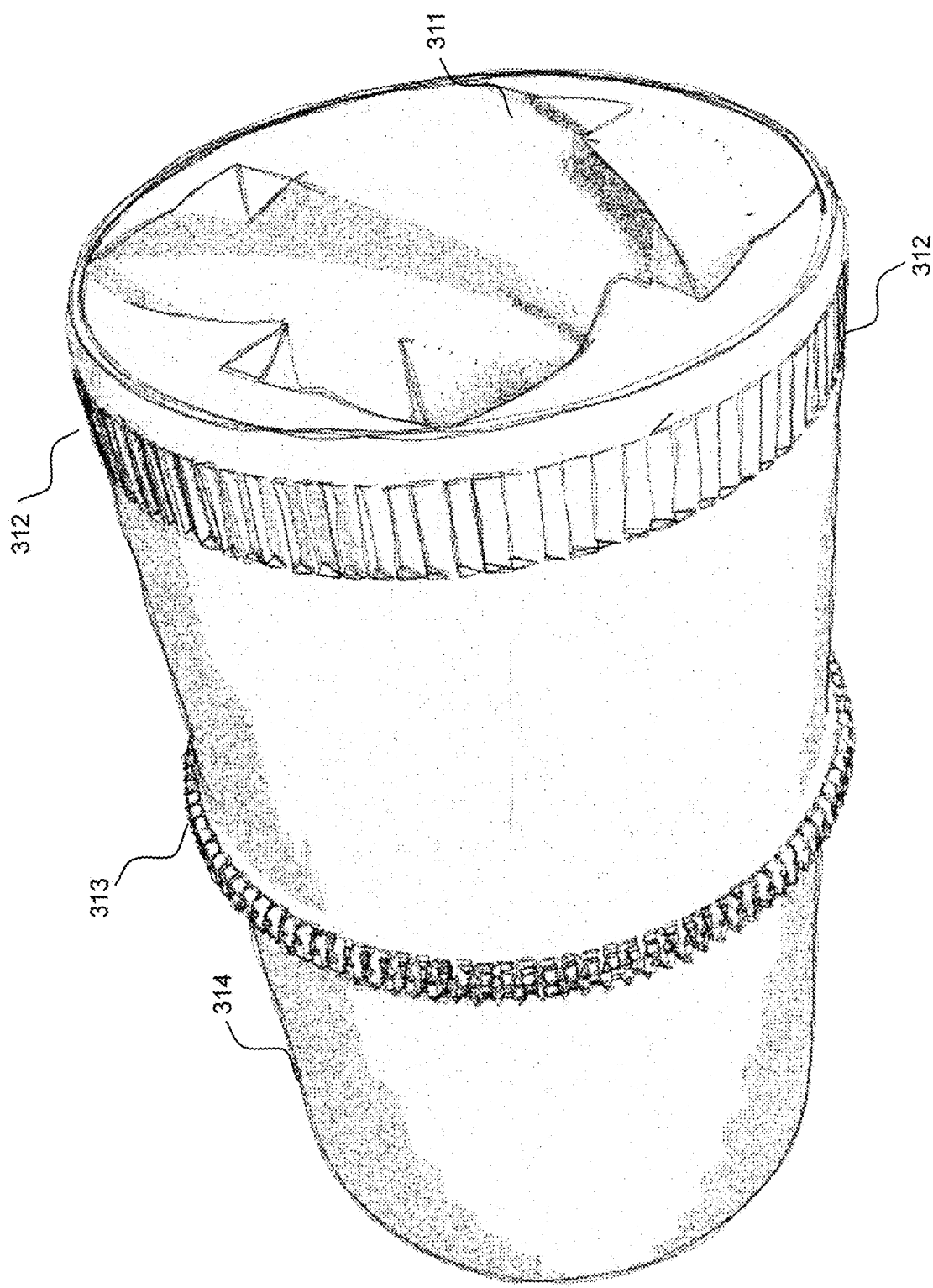

FIG. 3B is a rendering of the tube screw from the outside showing the notches/vibratory mechanism and an embedded gear. Vibratory ramped notches interface with a protrusion from the housing body causing an intermittent deflection in position of the tube.

Figure 4A:
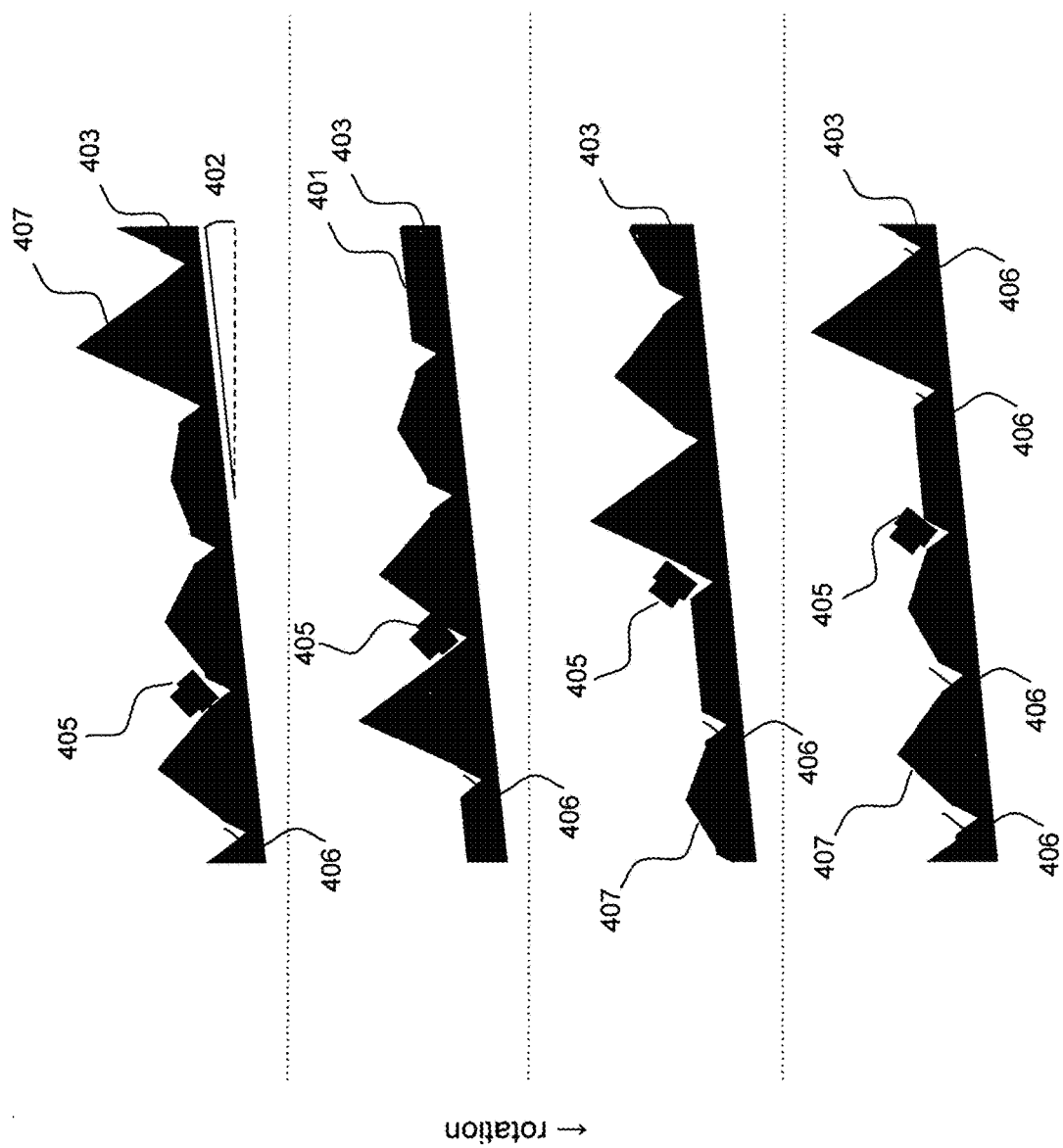

FIG. 4A is a length-wise, cross-sectional mock-up of the bottom-half of the tube screw in action with example small being propelled up a slope. As the tube rotates, small pieces move slowly in the shallow grooves.

FIG. 4B is a length-wise, cross-sectional mock-up of the bottom-half of the tube screw in action with example small and large pieces being propelled up in a slope. As the tube rotates, large pieces are repeatedly lifted up to slide forward.

Figure 5:
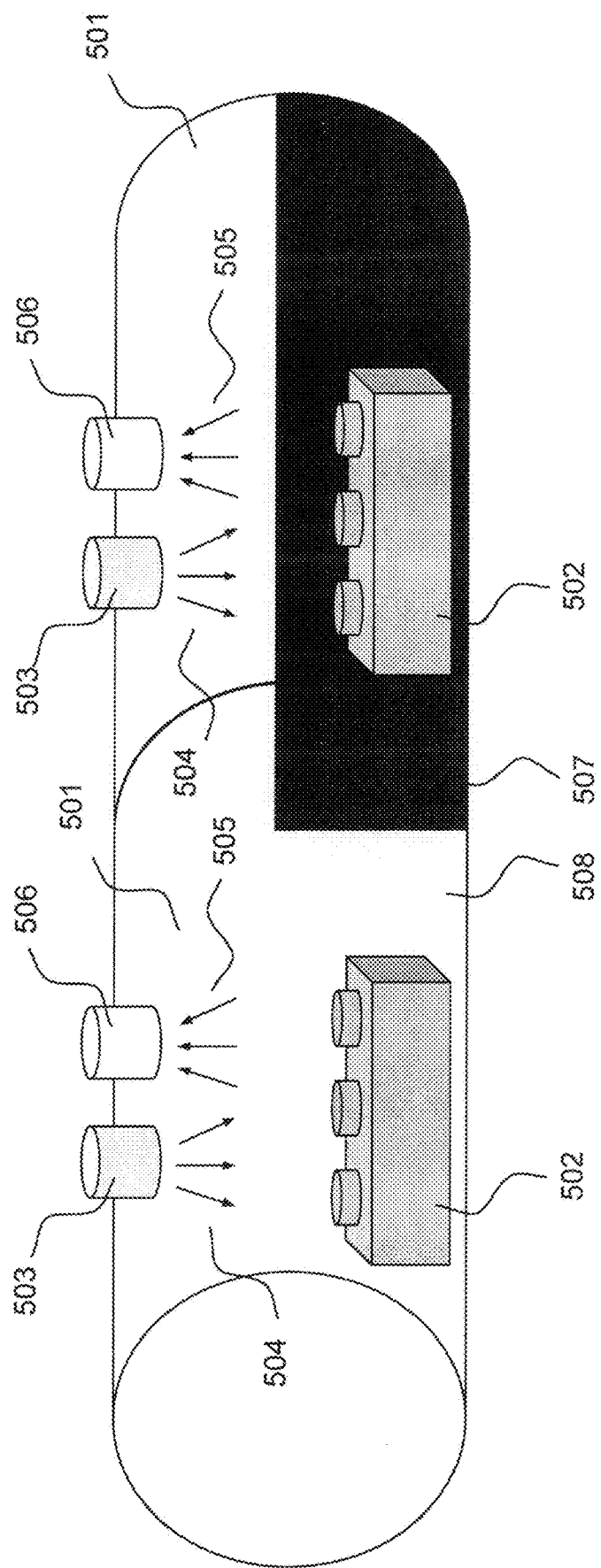

FIG. 5 is shows illumination and sensing. Using one or many controlled light sources, one or many sensors read back light intensity data. As pieces move by, the sensor readings change and are used to determine piece attributes or further actions.

Figure 6:
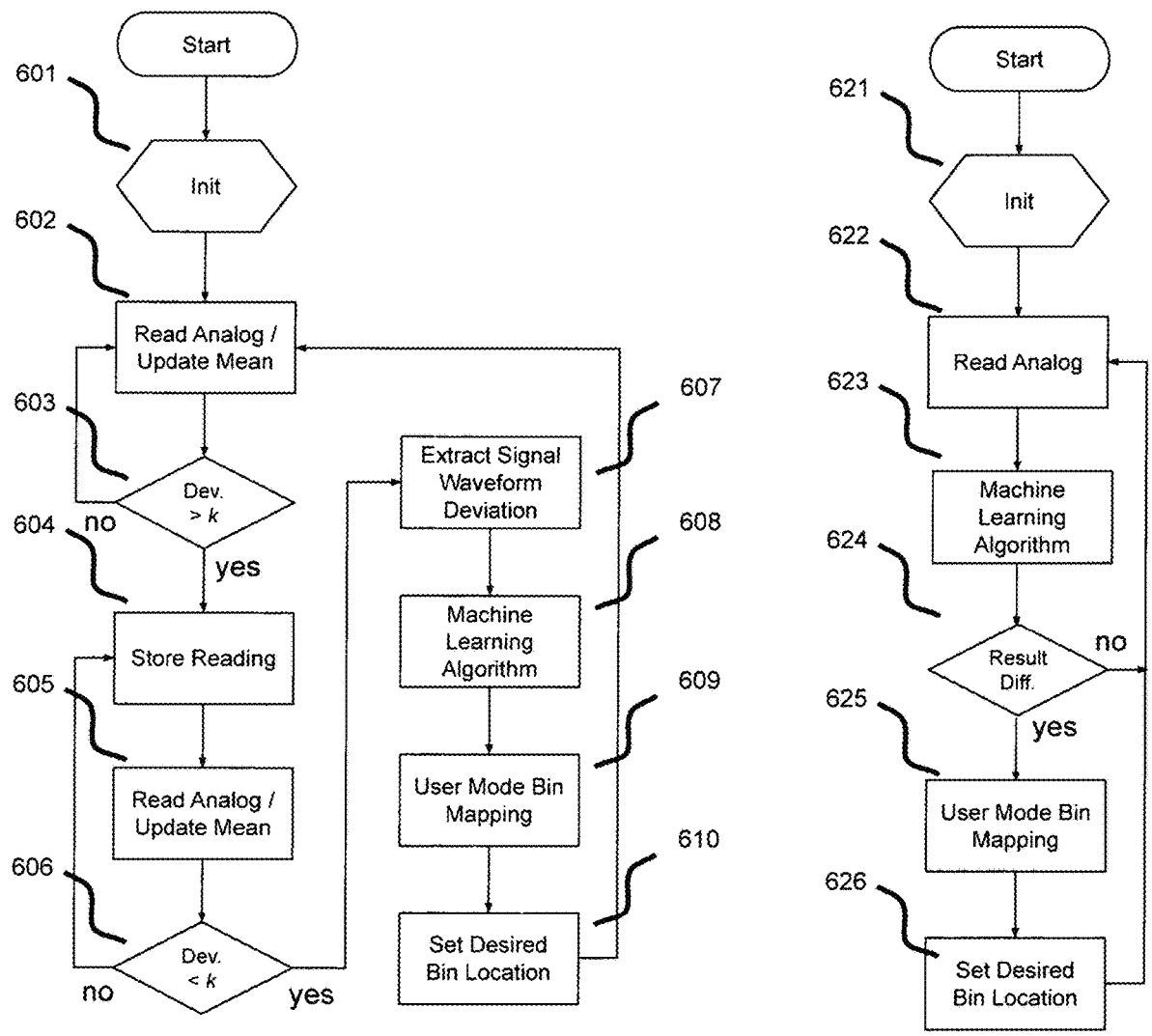

FIG. 6 is the high-level algorithm for the apparatus. New sensor readings are made continuously; depending on changes in the signal, the machine learning algorithm determines where to put the piece and/or what kind of piece it is.

FIG. 7 is a rendering of the keyed spigot with integrated gearing. The rotation of the spigot is measured by the effect the passing of the embedded magnets have on nearby sensors.

DETAILED DESCRIPTION OF THE INVENTION

Our sorter consists of five main subsystems working together to sort pieces: 1) hopper, 2) separation, 3) sensing, 4) processing and 5) binning. The user places pieces into the parts hopper where they flow to the separation stage as space becomes available. During separation, pieces are propelled until they have a sudden increase in speed that allows each piece to be sensed (and steered) separately. As parts pass by the sensors, the amount of each color component is sensed in the material. After sufficient processing time, the correct action is determined for that part. The part continues to travel toward one or more selection mechanisms which are positioned for the assigned bin, chute, or storage location (in the case of storage built into furniture). The part then drops into a temporary or final storage container or to the next stage of the selection mechanism. The implementation of this device has many embodiments consisting of differing mechanisms for propulsion of parts, separating pieces, sensing colors, computation, bin selection, and part storage.

The physical operation of the sorting device concerns the movement of the parts. In one embodiment, the parts are placed in a funnel-like hopper where gravity feeds parts towards a propulsion system as parts that were placed prior are moved. The design of the hopper is such that it constrains parts to only those parts that are expected to successfully fit through the entire machine. The hopper may additionally contain a stirring or lifting element to ensure parts continue to flow or to add potential energy for subsequent stages.

From the hopper, parts are propelled through the system with a sudden acceleration that markedly increases speed, which separates parts (103) from one another. One embodiment (see FIG. 1) uses two conveyors, where the first conveyor (101) is much slower than the second (102). A second implementation uses a slide that creates a single line of pieces and a single conveyor moving faster than the parts move on the slide. A third approach (see FIG. 2) uses two angles of slides (201, 205), the second (205) much steeper than the first (201)—vibration (203) may be used to get the parts (202, 204) to "walk" down the slides at speeds proportional to the slide angles. These mechanisms separate parts due to the motion being based on the forces acting on the center of gravity that are not exactly aligned. The relative differences in the positioning of that center are then amplified due to the temporary difference in speed of motion. The parts may additionally be constrained to a single-file line of parts by a narrowing or sloping as is used in standard feeder mechanisms, such as a bowl feeder.

In the fourth and preferred embodiment (see FIGS. 3A, 3B, 4A & 4B), a rotating tube (301, 314, 403, 413) with one or more shallow helical groove(s) (302, 311, 406, 416) is used like a screw to slowly move and line up individual pieces (405, 415), then each part falls (greatly accelerating them) one at a time onto a slide, speeding the piece's movement. The helical grooves in the interior of the tube allow for only a single piece (405) at each point along the root of the helical groove. When used at an inclination (402, 412) a build-up of pieces or excessively large pieces (i.e. >radius of the screw) will slide back down the tube on the flat crests of the helical screw (401), negating their progress. In the preferred embodiment, the grooves have a steep, approximately 90 degree angle, V-shape such that pieces can only get caught in a "single-file line" oriented along the screw helix. Another novel component of the invention are ramps (303, 407, 417) which lift large pieces (414) and propel them forward as the screw rotates. These ramps are overlaid on the crests of the shallow screw, between turns of each helical groove, so both small and large pieces can simultaneously be propelled. For this to be the case, the ramps are offset with a phase shift. To exaggerate this effect, the ramps are also shorter near the end of the tube. The result is that while the tube is inclined (412), the effective slope (411) from the ridge on one ramp to the next is downward. These ramps effectively act as a wedge, however, only for pieces large enough to span between them. The ramps are separated so that smaller pieces can slide in between them if they are not able to stay in the shallow grooves. One further detail of the tube screw, are notches (312) on the exterior that interact with a protuberance on the containing body to shake/vibrate/knock the tube to ensure parts are not stuck in unintended orientations and to prevent excess build ups of potential energy in the pieces as the tube rotates (in other words, the actions helps to overcome any static coefficient of friction). This helps to ensure pieces are expelled individually and slide smoothly along the groove or ramps. The tube may also have an integrated gear (313) to mesh with a motor or belt for rotating the tube. In addition, the lower end (or entrance) of the tube may contain a back-flow preventer which prevents pieces from sliding all the way out of the tube. An example of this is to have a narrow opening on the entrance of the tube (304).

The parts are sensed using emitted light (504) from a light source (503) in a controlled environment (501) and light to digital conversion sensors (506) and circuitry. One embodiment uses white light and a plurality of sensors with a plurality of differing wavelength filters. Another uses a plurality of differing color light sources and a sensor that passes all light in the visible spectrum. Multiple light sources may be used to assure proper illumination and is preferred. The sensors may be arrays such as camera chips, smaller light-to-digital converters possessing a dozen or so pixels, or individual photodiodes/phototransistors, which are preferred for their cost to performance in a low cost consumer device which prioritizes color based sorting. In shape identification applications, camera chips (arrays of pixel sensors) are preferred. These may include standard RGB arrays or sensors that are paired with specialized projectors such as time-of-flight or structured light 3D sensors. In each of these embodiments, data is gathered from position constrained light sensing devices. Those data are processed to detect attributes of interest in software such as color, shape, size, transparency, gloss, etc. and the presence or absence of a piece.

In the preferred embodiment (see FIG. 5), with multiple spectrum light sources (503) and broad spectrum photodiodes (506) (since LEDs are lower cost than PDs), each light color is cycled individually and the light reflected back is sampled. In the preferred implementation for propulsion, the parts (502) are moving such that they are "visible" to each sensor for approximately 10 to 400 ms (depending on part size and slope of the slide). As such sampling reflected red, green, and blue light requires cycling the light (504) and sampling the reflected light (505) at least 3× faster than the part is visible for. A standard PD amplifier circuit is used and sampled with an analog-to-digital converter (ADC).

After a short delay and continued movement, the parts reach the binning mechanism. Binning can be done in a variety of ways. One embodiment is a conveyor with air blades or paddles to push parts into the correct bins. A second embodiment uses multiple tiers of funnels or paddles that do m-ary selection in $\log_m(n)$ cascaded stages. Our preferred embodiment (for low cost), are rotating spigots (see FIG. 7) that are nearly inertially centered on the axis of rotation (so that motion can be quick with minimal effect on the stability of the platform). A motor is powered to move the spigot(s) (701) into position (610, 626). A single spigot can select from multiple bins or slides (that feed bins), enabling the use of a single motor (meshed with the integrated gear (702)) as opposed to cascaded stages of binary or ternary selection. Spigots or any other bin selection mechanism may be cascaded to select between any configurable number of destinations.

A spigot can spin freely and a keyed quadrature encoding of position can be used to know where it is pointed. General purpose solutions do not allow for keying, however, our application does (since not every position must be used and we do not need equal distribution of positions). While servos could be used instead, they are generally more expensive since they need to know absolute position. In addition, servos require additional manufacturing calibration procedures or parts that add cost. The keyed quadrature signal needs no calibration since the parts that need positioning contain the key itself. In one embodiment, the keyed quadrature signal can be generated using a pair of stop switches and a polygonal shape on the spigot. However, in the preferred embodiment a set of magnets (703) are used with hall effect sensors monitoring the position of magnets as they move by. One example of keying in this instance is a one or more consecutive "missing" magnets amongst a set of regularly distributed magnets.

Our algorithm (see FIG. 6) for detection of parts enables us to not use additional sensors (reducing cost). Instead, we use at least two different color backgrounds on which we sense color; here we prefer a white (508) and a black (507) background. The important aspect being that the color space is covered using different intensities of background for each color channel. This inventive step enables us to use the change from the mean in any one of the color signals as a sign of a part moving along even if it may blend in with the background of the other. It is important to note that the two backgrounds are instrumental in operation since the amount of ambient light could greatly affect these signals. Moreover, the preferred embodiment uses backgrounds that when passing pieces obscure will result in the opposite effect on the reflected light, increasing one and decreasing the other. A variational or patterned background may be substituted for a plurality of distinct backgrounds. An examples of varied or patterned backgrounds include a color or intensity gradient, or non-uniformly stretched checkerboard. In one embodiment, we frame the deviation from the anticipated color intensity (initialized, 601, as the first reading and continuously updated, 602, 605), or the mean, and excerpt a multi-millisecond sample of the signal as the part passes by (602-607). Each excerpt from each background and each emitted light color are processed with an artificial intelligence algorithm (608). Alternatively, the signal is processed continually (622-624) with each new sample, or set of samples, initiating processing which not only classifies but also acts as a detector. The preferred embodiment is a deep and/or recurrent neural network; other forms, such as a support vector machine or Gaussian mixture model, could also be used. In the case of the recurrent neural network, the last output of the algorithm may be used as an input. In which case, the output used as input is initialized (621) to be any valid output value.

The operation is based on the light intensity deviations in multiple components of the visible light spectrum (for example, red, green, and blue) as pieces pass known background reference colors. While the absolute magnitude of these light intensity deviations are important, the machine learning algorithm may find additional features embedded in those data to perform a more robust identification. Color is detected by the change in the red, green, and blue reflected light. Transparency is detected by the difference in the expectations of the change in each light component between a light background and a dark background. If a part is transparent, it's color may be identified by the responses seen on a white background, however, on a black background there may be no response, yet an opaque piece would still have an identifiable color response. Size (or apparent surface area, the area of the 3D objected projected into the view of the sensor) can be estimated, given the color, by using the duration and intensity of the deviation of multiple sensors a fixed distance apart. Using a table lookup, the users settings may determine the destination bin for a particular color, size, transparency, or shape part (609, 625) or any combination there of. However, the machine learning (ML) algorithm may be used to train a model to directly select the bin or predict the exact piece, rather than estimating attributes of the pieces. An exact piece is identifiable by the combination of the aforementioned properties, either directly or indirectly from the sensor readings. Determination of the groupings (of one or more types of) pieces is considered classification.

Given a window, new samples from a time-series, or image of digital color readings we can train a model using standard ML approaches. Here, we prefer a neural network that, given enough data, is capable of mitigating the detrimental effects of the specular properties of smooth plastic finishes, when attempting to determine the true color as opposed to the apparent color. If using a fixed window or image of data, a deep and/or convolutional neural network is preferred. If multiple time-steps are used, then a recurrent neural network (RNN) is preferred. If both an image and multiple time-steps are used, then a combination of approaches may be used. While training these models, the ML algorithm finds a mapping from the inputs to the desired outputs. Neural networks are known for being large and compute intensive in many applications. Thus, an efficient implementation is needed in microcontroller or embedded microprocessor applications.

A neural network classifier is embedded on a low cost microcontroller with an integer hardware multiply unit. The invention is not limited to any particular bit-width processor as the method can be adapted for the precision needed or available. To make the system efficient, during training, the neural network weights are constrained and regularized to spread the internal representations preventing any small subset of weights from dominating which would result in only a few weights being very large (and thus, others would round to zero using a low bit-width representation). This is important when deploying to a microcontroller, since we store values using the N-most significant bits that are used, which it determined by the largest weight value. The network is trained using standard methods on a development computer using floating-point arithmetic. Then the network weights are extracted, scaled up to fit the maximum amount of information in the desired word size, and converted to fixed point. The maximum weight norm and dropout ensure the spread of the weight values (such that the scale of any one weight is not much greater than others) so that accurate information can be held in just a few bits. Multi-word intermediate sums can be used if required, but are efficient on most microcontrollers. All activation and gating nonlinearities use piecewise linear functions which are highly efficient on microcontrollers. Final layers are not entirely implemented on device; rather, just the index of the peak value is found, dropping any need for complex operations, approximations, or relative calculations. To ensure, each operation is efficient, all numbers, thresholds, offsets, and weights are pre-scaled after training such that no scaling operations are duplicated at runtime except for activation and gating whose functions have bounded ranges.

These combinations of mechanisms and algorithms can be mated with bins, containers, slides, etc. to separate the pieces. They can also be devoid of binning and serve the purpose of counting or inventory, or other applications requiring piece separation such as ultraviolet (UV) light sterilization. For example, the above stated collection of mechanisms could be augmented to include illumination with UV light shining on the pieces as they are separated. Separation during light sterilization is desirable so that more of the surfaces of the pieces are exposed to the light. In particular, a hidden UV light is preferable since it leaves no lasting residue that children could be exposed to, while potentially reducing germ exposure between children. Given this range of applications, the category of the final/overall embodiment may range due to it's mounting; from furniture, to desktop device, to mobile robot, to industrial tool/machinery.

What is claimed is:

1. An apparatus comprising:
a tube wherein said tube has an outer and inner portion and said inner portion is hollow;
one or more grooves in the hollow inner portion and wherein said grooves extend axially and circumferentially;
a plurality of ramps on said hollow inner portion wherein said ramps extend inward toward the center of said tube above a crest formed longitudinally between said grooves, and said ramps increase and decrease in height circumferentially.

2. The apparatus of claim 1 further comprising:
notches on the outer portion of said tube.

3. The apparatus of claim 2 further comprising:
at least one protuberance in contact with said notches.

4. The apparatus of claim 1 wherein:
said tube is mounted such that it is rotatable.

5. The apparatus of claim 1 wherein:
at least one of said one or more grooves forms an approximately 90 degree angle.

6. The apparatus of claim 1 wherein:
at least one of said one or more grooves is in a "V" shape.

7. The apparatus of claim 1 wherein:
at least one ramp at one end of the tube is offset and shorter compared to at least one ramp at the other end of the tube.

8. The apparatus of claim 1 wherein:
the effective slope from the ridge on at least one ramp to at least one other ramp is downward.

9. The apparatus of claim 1 further comprising:
a gear embedded in the outer portion of the tube.

10. The apparatus of claim 1 further comprising:
a back-flow preventer on the inner portion of the tube.

11. An apparatus comprising:
a separator that separates one or more pieces such that each piece is individually detectable by one or more sensors;
said separator consists of a tube wherein said tube has an outer and inner portion and said inner portion is hollow, with one or more grooves in the hollow inner portion wherein said grooves extend axially and circumferentially, and a plurality of ramps on said hollow inner portion wherein said ramps extend inward toward the center of said tube above a crest formed longitudinally between said grooves, and said ramps increase and decrease in height circumferentially;
said one or more sensors measures reflected light on a plurality of differing backgrounds or on one or more backgrounds with variation;
one or more controllers are connected to said one or more sensors;
a controller that identifies at least one property or classification of the one or more pieces from said reflected light.

12. The apparatus of claim 11 further comprising:
a binning mechanism that places said one or more pieces into one of a plurality of bins based on one or more properties or the number of pieces detected prior.

13. The apparatus of claim 12 wherein said binning mechanism is selected from a group comprising:
a conveyor with air blades wherein said air blades propel said one or more pieces into said one of a plurality of bins;
paddles that propel said one or more pieces into said one of a plurality of bins;
one or more rotating spigots that drop one or more pieces into said one of a plurality of bins;
one or more funnels that drop one or more pieces into said one of a plurality of bins.

14. The apparatus of claim 12 further comprising:
a storage that holds one or more pieces.

15. The apparatus of claim 11 wherein said controller detects the presence of one or more pieces using the deviations in the reflected light;
a controller that changes a display based on the number of pieces.

16. The apparatus of claim 11 further comprising:
a hopper wherein said hopper is constrained to block pieces at the opening that will not fit thru the entire apparatus.

17. The apparatus of claim 11 further comprising:
an illumination-based sterilization source.

* * * * *